(12) United States Patent
Xiao et al.

(10) Patent No.: US 10,279,959 B2
(45) Date of Patent: May 7, 2019

(54) ALKOXYSILYLAMINE COMPOUNDS AND APPLICATIONS THEREOF

(71) Applicant: AIR PRODUCTS AND CHEMICALS, INC., Allentown, PA (US)

(72) Inventors: Manchao Xiao, San Diego, CA (US); Ronald Martin Pearlstein, San Marcos, CA (US); Richard Ho, Mira Loma, CA (US); Daniel P. Spence, Carlsbad, CA (US); Xinjian Lei, Vista, CA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 1326 days.

(21) Appl. No.: 14/096,388

(22) Filed: Dec. 4, 2013

(65) Prior Publication Data

US 2014/0158580 A1   Jun. 12, 2014

Related U.S. Application Data

(60) Provisional application No. 61/735,793, filed on Dec. 11, 2012.

(51) Int. Cl.
| | | |
|---|---|---|
| *C07F 7/10* | (2006.01) |
| *B65D 25/14* | (2006.01) |
| *C23C 16/00* | (2006.01) |
| *C07F 7/18* | (2006.01) |

(52) U.S. Cl.
CPC ............. *B65D 25/14* (2013.01); *C07F 7/10* (2013.01); *C07F 7/1804* (2013.01); *C23C 16/00* (2013.01)

(58) Field of Classification Search
CPC .......... C07F 7/10; C07F 7/1804; C23C 16/00; B65D 25/14
USPC ........... 556/412; 427/255.28, 578; 206/524.3
See application file for complete search history.

(56) References Cited

U.S. PATENT DOCUMENTS

| | | | |
|---|---|---|---|
| 3,054,818 A | 9/1962 | Pepe et al. | |
| 7,314,506 B2 | 1/2008 | Vininski et al. | |
| 7,425,350 B2 | 9/2008 | Todd | |
| 7,498,273 B2* | 3/2009 | Mallick | C23C 16/045 257/E21.17 |
| 7,524,735 B1 | 4/2009 | Gauri et al. | |
| 7,582,555 B1 | 9/2009 | Lang et al. | |
| 7,629,227 B1 | 12/2009 | Wang et al. | |
| 7,888,233 B1 | 2/2011 | Gauri et al. | |
| 7,888,273 B1 | 2/2011 | Wang et al. | |
| 7,915,139 B1 | 3/2011 | Lang et al. | |
| 7,943,531 B2 | 5/2011 | Nemani et al. | |
| 8,187,951 B1 | 5/2012 | Wang et al. | |
| 2006/0247404 A1 | 11/2006 | Todd | |
| 2011/0151678 A1 | 6/2011 | Ashtiani et al. | |

FOREIGN PATENT DOCUMENTS

| | | |
|---|---|---|
| DE | 1158973 B | 12/1963 |
| EP | 2660041 | 11/2013 |
| KR | 10-2010-0012092 | 2/2010 |
| KR | 10-2010-0036186 | 4/2010 |
| KR | 10-2010-0085993 | 7/2010 |

OTHER PUBLICATIONS

Ulrich Wannagat et al, Symmetrical mixed substituted trisilyannines . . . , Mh Chem., vol. 95, Jan. 1, 1963, pp. 39-44.
Ulrich Wannagat et al, Tris-[trialkoxysilyl]-amines and related compounds [1], Institute of Inorg. Chem. at Graz Univ. of Tech., Jan. 1, 1963, vol. 75, No. 1, pp. 95-95.
Ulrich Wannagat et al, The selective splitting of cyclosilazanes with alcohols and with hydrogen chloride, Jan. 1, 1964, Mh. Chem., vol. 95, pp. 801-811.
Ulrich Wannagat et al, Some reactions of phenoxy-amino-silanes with alkali amides, Jan. 1, 1968, Mh Chem., vol. 99, pp. 1372-1375.
Ulrich Wannagat et al, Some new silylamines, disilazanes and cyclosiloxazanes, Jan. 1, 1965, Mh. Chem., vol. 96, pp. 587-592.
M. Elsheikh, et al, "Evidence for Silicon-Carbon and Silicon-Nitrogen Multiple-Bonded Intermediates from Photolysis", Journal of the American Chemical Society, 1979, 2491-2492.
O.J. Scherer, et al, "Silicium-Stickstoff-Heterocyclen mit C=N-Doppelbindungen", Angewandte Chemie, 1967, 60-61.
Reaxys print out, 2015, 1-13.
L. Hench, et al, The Sol-Gel Process, American Chemical Society, 1990, 33-72.
J. Wannagat, et al, "Einige asymmetrisch substituierte Tris-[alkoxyorganylsilyl]-amine", Monatshefte fur Chemie, 1965, 593-596.
Von Dr. K. Schwochau, et al, "Darstellung, Eigenschaften und Kristallstruktur von Kalium-hexafluorotechnetat (IV)", Angewandte Chemie, 1962, 95.

* cited by examiner

*Primary Examiner* — Pancham Bakshi
(74) *Attorney, Agent, or Firm* — Rosaleen P. Morris-Oskanian; Joseph D. Rossi

(57) ABSTRACT

Described herein are alkoxysilylamine precursors having the following Formulae A and B:

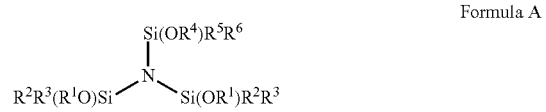

Formula A

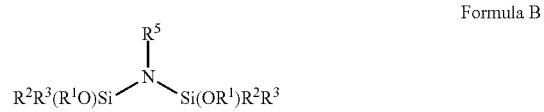

Formula B wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^4$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, a $C_6$ to $C_{10}$ aryl group, and a linear or branched $C_1$ to $C_{10}$ alkoxy group. Also described herein are deposition processes using at least one precursor have Formulae A and/or B described herein.

2 Claims, 1 Drawing Sheet

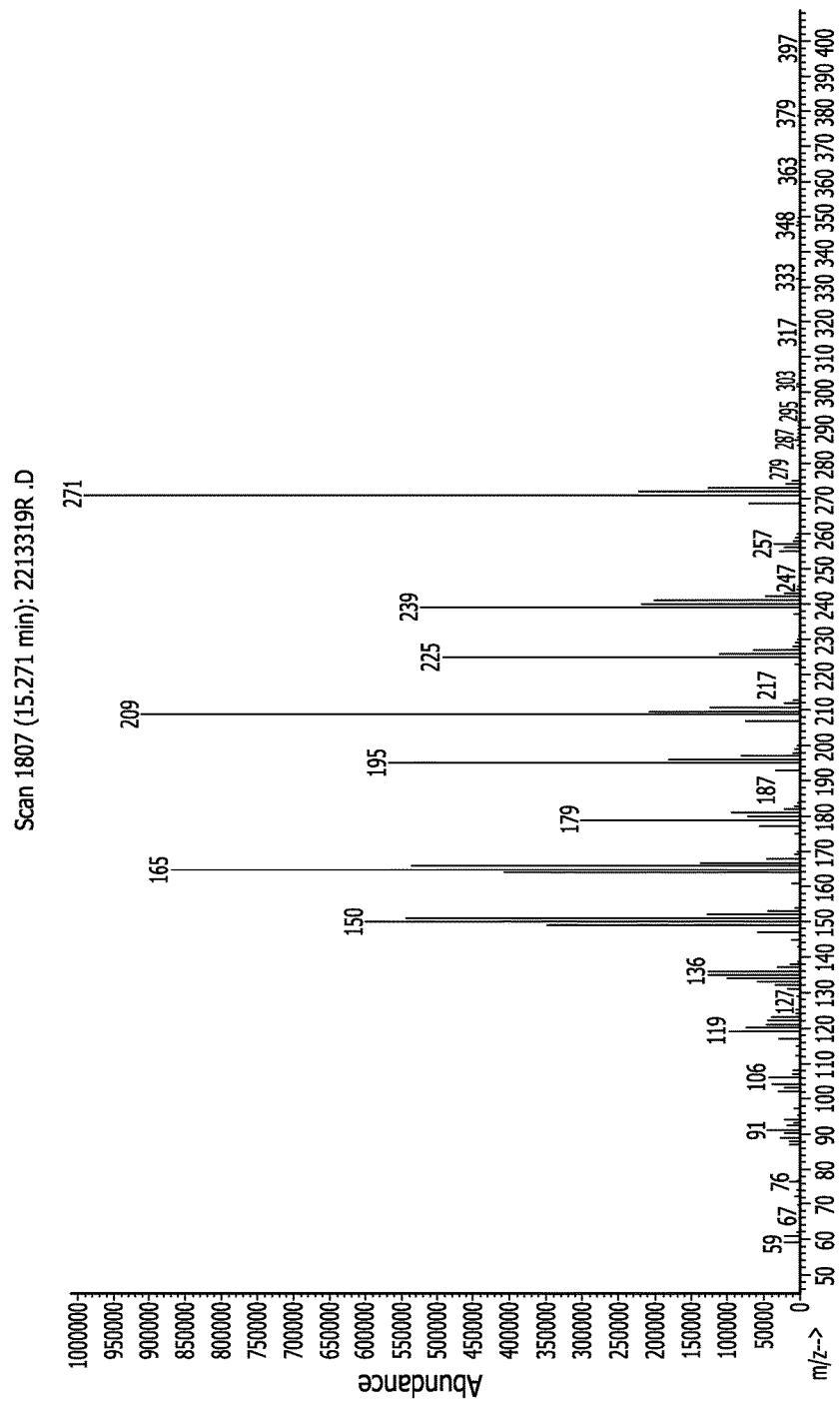

ALKOXYSILYLAMINE COMPOUNDS AND APPLICATIONS THEREOF

CROSS REFERENCE TO RELATED PATENT APPLICATIONS

The present patent application claims the priority benefit of U.S. patent application Ser. No. 61/735,793, filed 11 Dec. 2012.

BACKGROUND OF THE INVENTION

Described herein are alkoxysilylamine compounds, more specifically, alkoxysilylamine compounds such as tris(alkoxysilyl)amine or bis(alkoxysilyl)amine compounds, and the use of these compounds for the deposition of silicon and silicon-containing films such as silicon oxide, silicon oxynitride, silicon carboxide, silicon oxycarbonitride and silicon carboxynitride films.

US2011151678A discloses novel gap fill schemes involving depositing both flowable oxide films and high density plasma chemical vapor deposition oxide (HDP oxide) films. According to various embodiments, the flowable oxide films may be used as a sacrificial layer and/or as a material for bottom up gap fill. In certain embodiments, the top surface of the filled gap is an HDP oxide film. The resulting filled gap contains HDP oxide film or a combination of HDP oxide and flowable oxide films.

U.S. Pat. Nos. 7,524,735B, 7,582,555B, 7,888,233B, and 7,915,139B disclose methods related to filling gaps on substrates with a solid dielectric material by forming a flowable film in the gap. The flowable film is then converted to a solid dielectric material. In this manner, gaps on the substrate are filled with a solid dielectric material. According to various embodiments, the methods involve reacting a dielectric precursor with an oxidant to form the dielectric material. In certain embodiments, the dielectric precursor condenses and subsequently reacts with the oxidant to form dielectric material. In certain embodiments, vapor phase reactants react to form a condensed flowable film.

U.S. Pat. No. 7,943,531B discloses a method of depositing a silicon oxide layer over a substrate includes providing a substrate to a deposition chamber. A first silicon-containing precursor a second silicon-containing precursor and a NH$_3$ plasma are reacted to form a silicon oxide layer. The first silicon-containing precursor includes at least one of a Si—H bond and a Si—Si bond. The second silicon-containing precursor includes at least one Si—N bond. The deposited silicon oxide layer is subsequently annealed.

U.S. Pat. No. 7,425,350 B discloses a method for making a silicon-containing ("Si-containing") material comprises transporting a pyrolyzed Si-precursor to a substrate and polymerizing the pyrolyzed Si-precursor on the substrate to form a Si-containing film. Polymerization of the pyrolyzed Si-precursor may be carried out in the presence of a porogen to thereby form a porogen-containing Si-containing film. The porogen may be removed from the porogen-containing Si-containing film to thereby form a porous Si-containing film. Preferred porous Si-containing films have low dielectric constant and thus are suitable for various low dielectric constant or low-k applications such as in microelectronics and microelectromechanical systems.

U.S. Pat. Nos. 7,888,273B, 7,629,227B and 8,187,951BA disclose methods of lining and/or filling gaps on a substrate by creating flowable silicon oxide-containing films are provided. The methods involve introducing vapor-phase silicon-containing precursor and oxidant reactants into a reaction chamber containing the substrate under conditions such that a condensed flowable film is formed on the substrate. The flowable film at least partially fills gaps on the substrates and is then converted into a silicon oxide film. In certain embodiments the methods involve using a catalyst (e.g. a nucleophile or onium catalyst) in the formation of the film. The catalyst may be incorporated into one of the reactants and/or introduced as a separate reactant. Also provided are methods of converting the flowable film to a solid dielectric film. The methods of this invention may be used to line or fill high aspect ratio gaps including gaps having aspect ratios ranging from 3:1 to 10:1.

Thus, there is a need to develop novel alkoxysilylamines to deposit silicon or silicon-containing films such as silicon oxide, silicon oxynitride, silicon carboxide, silicon oxycarbonitride and silicon carboxynitride films by employing chemical vapor deposition, atomic layer deposition or flowable chemical vapor deposition. Described herein provides are alkoxysilylamine compounds that will meet these demands.

BRIEF SUMMARY OF THE INVENTION

In one aspect, described herein are alkoxysilylamine compounds such as tris(alkoxysilyl)amine having a general formula:

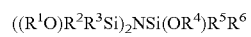

or bis(alkoxysilyl)amine compounds having a general formula:

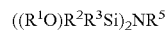

wherein $R^1$ and $R^4$ are each independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, $R^5$, and $R^6$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

In another aspect, described herein are tris(alkoxysilyl)amine or bis(alkoxysilyl)amine compounds having the following general Formulae A or B:

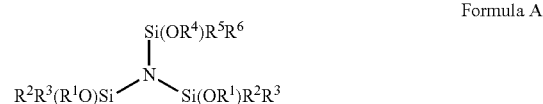

Formula A

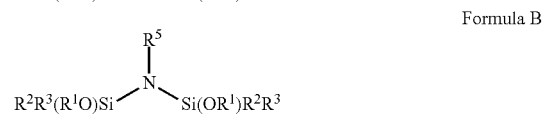

Formula B wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, $R^5$, and $R^6$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

Also described herein are deposition processes such as, without limitation chemical vapor deposition (CVD) or atomic layer deposition (ALD) processes, employing a tris(alkoxysilyl)amine precursor having the following general formula:

$$((R^1O)R^2R^3Si)_2NSi(OR^4)R^5R^6$$

wherein $R^1$ and $R^4$ are each independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, $R^5$, and $R^6$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

Also described herein are deposition processes such as, without limitation chemical vapor deposition (CVD) or atomic layer deposition (ALD) processes, employing a bis(alkoxysilyl)amine precursor having the following general formula:

$$((R^1O)R^2R^3Si)_2NR^5$$

wherein $R^1$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, and $R^5$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

BRIEF DESCRIPTION OF SEVERAL VIEWS OF THE DRAWINGS

FIG. 1 shows the mass spectrum of the compound tris(dimethoxysilyl)amine of Example 1.

DETAILED DESCRIPTION OF THE INVENTION

Described herein are alkoxysilylamine, more specifically, tris(alkoxysilyl)amine or bis(alkoxysilyl)amine compounds, that can be used as precursors in deposition processes to form stoichiometric and non-stoichiometric silicon and silicon containing films such as, but not limited to, silicon oxide, silicon oxycarbide, silicon nitride, silicon oxynitride and silicon oxycarbonitride. The deposition processes include, but are not limited to, chemical vapor deposition (CVD), plasma enhanced chemical vapor deposition (PECVD), cyclic chemical vapor deposition (CCVD), flowable chemical vapor deposition (FCVD), atomic layer deposition (ALD), or plasma enhanced atomic layer deposition (PEALD) processes.

The alkoxysilylamine precursors described herein are typically high purity volatile liquid precursors that are vaporized and delivered to a deposition chamber or reactor as a gas to deposit a silicon containing film via various deposition techniques including, but not limited to, chemical vapor deposition (CVD), cyclic chemical vapor deposition (CCVD), flowable chemical vapor deposition (FCVD), atomic layer deposition (ALD) for semiconductor devices. In other embodiments, the alkoxyaminosilane precursors can be used in a liquid-based deposition or film formation method such as, but not limited to, spin-on, dip coat, aerosol, ink jet, screen printing or spray application processes.

The selection of precursor materials for deposition depends upon the desired resultant dielectric material or film. For example, a precursor material may be chosen for its content of chemical elements, its stoichiometric ratios of the chemical elements, and/or the resultant dielectric film or coating that are formed under afore-mentioned deposition techniques.

The precursor material may also be chosen for various other characteristics such as cost, non-toxicity, handling characteristics, volatility, thermal stability, compatibility with other silicon containing precursors, and/or other considerations. In certain embodiments, the precursors having the general formula or Formulae A and/or B described herein comprise less than 2% by weight, or less than 1% by weight, or less than 0.5% by weight of by-product after being stored for a 6 months or greater, or one year or greater time period which is indicative of being shelf stable. In addition to the foregoing advantages, in certain embodiments, such as for depositing a silicon oxide or silicon nitride film using an ALD or PEALD deposition method, precursor described herein may be able to deposit high density materials at relatively low deposition temperatures, e.g., 500° C. or less, or 400° C. or less, 300° C. or less, 200° C. or less, 100° C. or less, or 50° C. or less.

As previously mentioned, described herein are alkoxysilylamine compounds, more specifically tris(alkoxysilyl)aminecompounds having the following general formula:

$$((R^1O)R^2R^3Si)_2NSi(OR^4)R^5R^6$$

wherein $R^1$ and $R^4$ are each independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, $R^5$, and $R^6$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

In another embodiment, also described herein are alkoxysilylamine compounds, more specifically bis(alkoxysilyl)amine compounds having the following general formula:

$$((R^1O)R^2R^3Si)_2NR^5$$

wherein $R^1$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and $R^2$, $R^3$, and $R^5$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

In another embodiment, described herein are at least one alkoxysilylamine which are the tris(alkoxysilyl)amine or bis(alkoxysilyl)amine precursors having Formulae A and B:

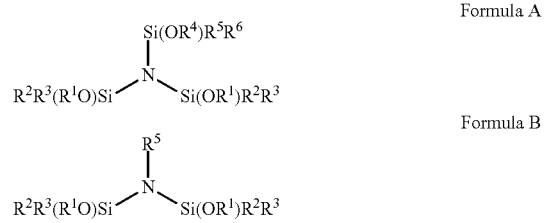

wherein $R^1$ and $R^4$ are each independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; and $R^2$, $R^3$, $R^5$, and $R^6$ are each independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group.

In one embodiment of Formula A, $R^1$ and $R^4$ are independently selected from a methyl or an ethyl group and $R^2$, $R^3$, $R^4$, $R^5$ are each independently selected from hydrogen or a $C_1$ to $C_5$ alkoxy group such as methoxy, ethoxy, iso-propoxy, n-propoxy, tert-butoxy, iso-butoxy, and sec-butoxy. In one particular embodiment, $R^2$, $R^3$, $R^4$ and $R^5$ are hydrogen or methoxy. In another embodiment, $R^1$ and $R^4$ are independently selected from branched alkyl groups such as, but not limited to, tert-butyl and tert-amyl and $R^2$, $R^3$, $R^4$, and $R^5$ are each independently selected from hydrogen, $C_1$ to $C_5$ alkyl groups such as methyl, ethyl, iso-propyl, sec-butyl, iso-butyl, tert-butyl, and tert-pentyl, preferably methyl or ethyl. Exemplary compounds having Formula A include, but are not limited to, $((MeO)_2HSi)_3N$, $((EtO)_2HSi)_3$ N, $((MeO)_2MeSi)_3N$, $((EtO)_2MeSi)_3N$, $((MeO)MeHSi)_3N$, $((EtO)MeHSi)_3N$, $((MeO)_2HSi)_2NSiH_2(OBu^t)$, $((EtO)_2HSi)_2 NSiH_2(OBu^t)$, $((MeO)_2HSi)_2NSiH(OEt)_2$, and $(^tBuO)H_2Si)_3N$. Exemplary compounds having Formula B include, but are not limited to, $((MeO)_2HSi)_2NH$, $((EtO)_2HSi)_2NH$, $((MeO)_2MeSi)_2NH$, $((EtO)_2MeSi)_2NH$, $((MeO)MeHSi)_2$ NH, $((EtO)MeHSi)_2NH$, $((MeO)_2HSi)_2NMe$, $((EtO)_2HSi)_2$ NMe, $((MeO)_2MeSi)_2NMe$, $((EtO)_2MeSi)_2$ NMe, $((MeO)MeHSi)_2NMe$, $((EtO)MeHSi)_2NMe$, $((MeO)_2HSi)_2NEt$, $((EtO)_2HSi)_2NEt$, $((MeO)_2MeSi)_2NEt$, $((EtO)_2MeSi)_2NEt$, $((MeO)MeHSi)_2NEt$, $((EtO)MeHSi)_2NEt$, $((MeO)_2HSi)_2NPr^n$, $((EtO)_2HSi)_2NPr^n$, $((MeO)_2MeSi)_2NPr^n$, $((EtO)_2MeSi)_2NPr^n$, $((MeO)MeHSi)_2NPr^n$, $((EtO)MeHSi)_2NPr^n$, $((MeO)_2HSi)_2NPr^i$, $((EtO)_2HSi)_2NPr^i$, $((MeO)_2MeSi)_2NPr^i$, $((EtO)_2MeSi)_2NPr^i$, $((MeO)MeHSi)_2NPr^i$, $((EtO)MeHSi)_2NPr^i$, $((MeO)_2HSi)_2NBu^t$, $((EtO)_2HSi)_2 NBu^t$, $((MeO)_2MeSi)_2NBu^t$, $((EtO)_2MeSi)_2NBu^t$, $((MeO)MeHSi)_2NBu^t$, $((EtO)MeHSi)_2NBu^t$, Certain key features of the tris(alkoxysilyl)amine or bis(alkoxysilyl)amine compounds described herein are the compounds contain at least one of the following bonds: Si—N, Si—O, and/or Si—H bonds which allow them to chemically react on substrate surfaces during a vapor deposition process and as a result, deposie silicon-containing films with certain properties which otherwise would not be possible for other organosilicon compounds under similar deposition conditions.

Throughout the description, the term "alkyl" denotes a linear, or branched functional group having from 1 to 10 or 1 to 4 carbon atoms. Exemplary alkyl groups include, but are not limited to, methyl, ethyl, n-propyl, isopropyl, n-butyl, isobutyl, sec-butyl, tert-butyl, n-pentyl, iso-pentyl, tert-pentyl, hexyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto. The term "cyclic alkyl" denotes a cyclic functional group having from 3 to 12 or from 4 to 10 carbon atoms. Exemplary cyclic alkyl groups include, but are not limited to, cyclobutyl, cyclopentyl, cyclohexyl, and cyclooctyl groups. The term "aryl" denotes an aromatic cyclic functional group having from 4 to 12 carbon atoms. Exemplary aryl groups include, but are not limited to, phenyl, benzyl, chlorobenzyl, tolyl, and o-xylyl. The term "alkenyl group" denotes a group which has one or more carbon-carbon double bonds and has from 2 to 12 or from 2 to 6 carbon atoms. Exemplary alkenyl groups include, but are not limited to, vinyl or allyl groups. The term "alkynyl group" denotes a group which has one or more carbon-carbon triple bonds and has from 2 to 12 or from 2 to 6 carbon atoms. The term "alkoxy" denotes an alkyl group which has is linked to an oxygen atom (e.g., R—O) and may have from 1 to 12, or from 1 to 6 carbon atoms. Exemplary alkoxy groups include, but are not limited to, methoxy (—OCH$_3$), ethoxy(—OCH$_2$CH$_3$), n-propoxy (—OCH$_2$CH$_2$CH$_3$), and iso-propoxy (—OCHMe$_2$).

The following Equations 1 to 4 provide examples of reaction schemes or synthesis routes which may be used to make the tris(alkoxysilyl)amines having the general formula or Formula A described herein.

(1)

(2)
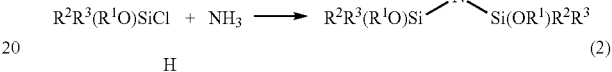

(3)
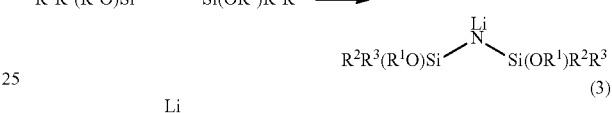

(4)
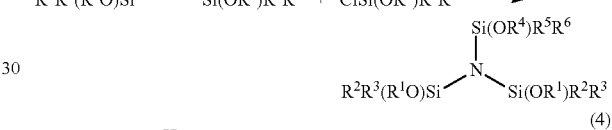

The reactions in Equations 1 to 4 can be conducted with (e.g., in the presence of) or without organic solvents. In embodiments wherein an organic solvent is used, examples of suitable organic solvents include, but are not limited to, hydrocarbon such as hexanes, octane, toluene, and ethers such as diethylether, and tetrahydrofuran (THF). In these or other embodiments, the reaction temperature is in the range of from about −70° to −20° C. to the boiling point of the solvent employed if a solvent is involved. The resulting tris(alkoxysilyl)amines can be purified via vacuum distillation after removing all by-products as well as solvent(s). Equations 1, 2 and 3 are embodiments involving reaction of alkoxychlorosilane with ammonia (eq (1)) to provide alkoxysilazane which is reaction with metal alkyl such as n-butyl lithium (eq (2)) to form lithium amide, followed by reaction with alkoxychlorosilane (eq (3)) to produce tris(alkoxysilyl) amine as product. The multi-step syntheses process described herein not only provide for the formation of tris(alkoxysilyl)amines containing the same alkoxylsilyl groups as substitutents such as $((MeO)_2HSi)_3N$, $((MeO)_2MeSi)_3N$, $((EtO)_2MeSi)_3N$, $((MeO)MeHSi)_3N$, $((EtO)MeHSi)_3N$, or $((^tBuO)H_2Si)_3N$ but also tris(alkoxysilyl)amines containing different alkoxysilyl groups as substituents such as $((MeO)_2HSi)_2NSiH_2(OBu^t)$, $((MeO)_2HSi)_2NSiH(OEt)_2$.

Another aspect of this invention is a mixture of the above general formula or Formulae A, B or combination thereof with a compatible silicon-containing precursor selected from the group consisting of dialkylaminosilanes, alkoxysilanes, dialkylaminoalkylsilanes, and alkoxyalkylsilanes. Examples of silicon-containing precursors include, but not limited to, bis(tert-butylamino)silane (BTBAS), tris(dimethylamino)silane (TRDMAS), tetraethoxysilane (TEOS), triethoxysilane (TES), di-tert-butoxysilane (DTBOS), di-tert-pentoxysilane (DTPOS), methyltriethoxysilane (MTES), tetramethoxysilane (TMOS), trimethoxysilane (TMOS), methyltrimethoxysilane (MTMOS), di-tert-butoxymethylsilane, di-tert-butoxyethylsilane, di-tert-pentoxymethylsilane, and di-tert-pentoxyethylsilane.

In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

It is believed that the tris(alkoxysilyl)amine or bis(alkoxysilyl)amine precursors described herein may provide better reactivity towards substrate surface during chemical vapor deposition, particularly CVD deposition or flowable CVD deposition to form Si—N—Si linkage or Si—O—Si linkage due to their chemical characteristics such as Si—H, Si—OR, Si—N—Si bonds. In addition to the foregoing advantages, in certain embodiments such as for depositing a silicon oxide or silicon oxynitride film using a cyclic CVD, an ALD, or PEALD deposition method, the tris(alkoxysilyl)amine or bis(alkoxysilyl)amine precursor described herein may be able to deposit high density materials at relatively low deposition temperatures, e.g., 500° C. or less, or 400° C. or less, 300° C. or less, 200° C. or less, 100° C. or less, or 50° C. or less.

In other embodiments such as for depositing a silicon oxide using typical FCVD processes, the tris(alkoxysilyl) amine or bis(alkoxysilyl)amine precursor described herein may be used in combination with other silicon containing precursors as a catalyst due to release of organoamine or ammonia as in situ catalyst at relatively low deposition temperatures, e.g., at 100° C. or less, 50° C. or less, 20° C. or less, even 0° C. or lower.

The deposition method used to form the silicon-containing dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition (PECVD), high density PECVD, photon assisted CVD, plasma-photon assisted (PPECVD), cryogenic chemical vapor deposition, chemical assisted vapor deposition, hot-filament chemical vapor deposition, CVD of a liquid polymer precursor, deposition from supercritical fluids, and low energy CVD (LECVD), and flowable chemical vapor deposition.

As used herein, the term "chemical vapor deposition processes" refers to any process wherein a substrate is exposed to one or more volatile precursors, which react and/or decompose on the substrate surface to produce the desired deposition.

As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator.

In one embodiment, the dielectric film is deposited using an ALD process. In another embodiment, the dielectric film is deposited using a CCVD process. In a further embodiment, the dielectric film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the dielectric film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors or non-halogenated other than the tris(alkoxysilyl)amine or bis(alkoxysilyl)amine precursors in formulae A and B. Examples of additional silicon-containing precursors include, but are not limited to, monoaminosilane (e.g., di-iso-propylaminosilane, di-sec-butylaminosilane, phenylmethylaminosilane; organo-silicon compounds such as trisilylamine (TSA); monoaminosilane (di-iso-propylaminosilane, di-sec-butylaminosilane, phenylmethylaminosilane); siloxanes (e.g., hexamethyl disiloxane (HMDSO) and dimethyl siloxane (DMSO)); organosilanes (e.g., methylsilane, dimethylsilane, diethylsilane, vinyl trimethylsilane, trimethylsilane, tetramethylsilane, ethylsilane, disilylmethane, 2,4-disilapentane, 1,4-disilabutane, 2,5-disilahexane, 2,2-disilylpropane, 1,3,5-trisilacyclohexane and fluorinated derivatives of these compounds); phenyl-containing organo-silicon compounds (e.g., dimethylphenylsilane and diphenylmethylsilane); alkoxysilanes include, but are not limited to, tetraethoxysilane (TEOS), triethoxysilane (TES), di-tert-butoxysilane (DTBOS), di-tert-pentoxysilane (DTPOS); oxygen-containing organo-silicon compounds ,e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4, 6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5, 7,9-pentamethylcyclopentasiloxane; hexamethoxydisiloxane, and fluorinated derivatives of these compounds.

Depending upon the deposition method, in certain embodiments, tris(alkoxysilyl)amine or bis(alkoxysilyl)amine precursors, other silicon-containing precursors may be introduced into the reactor at a predetermined molar volume, or from about 0.1 to about 1000 micromoles. In this or other embodiments, the tris(alkoxysilyl)amine or bis(alkoxysilyl) amine precursor(s) may be introduced into the reactor for a predetermined time period. In certain embodiments, the time period ranges from about 0.001 to about 500 seconds.

In certain embodiments, the dielectric films deposited using the methods described herein are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water, a mixture comprises water and an organic liquid), hydrogen peroxide ($H_2O_2$), oxygen ($O_2$), oxygen plasma, ozone ($O_3$), $N_2O$, NO, $NO_2$, carbon monoxide (CO), carbon dioxide ($CO_2$) and combinations thereof. For those embodiments wherein the mixture comprises water and an organic liquid, the organic liquid in the mixture can be selected from hydrocarbon, aromatic hydrocarbon, ether, amine, ketone, ester, organic acid, and organic amide. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited silicon-containing film.

In certain embodiments, the silicon-containing films comprise silicon and nitrogen. In these embodiments, the silicon-containing films deposited using the methods described herein are formed in the presence of nitrogen-containing source. A nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting silicon-containing film.

Energy is applied to the at least one of the precursor, nitrogen-containing source, reducing agent, other precursors or combination thereof to induce reaction and to form the silicon-containing film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The tris(alkoxysilyl)amine or bis(alkoxysilyl)amine precursor and/or other silicon-containing precursors may be delivered to the reaction chamber, such as a CVD or ALD reactor, in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the tris(alkoxysilyl)amine precursor, bis(alkoxysilyl)amine precursor, or both tris(alkoxysilyl)amine precursor and bis(alkoxysilyl)amine precursor is used in a composition comprising a solvent, the solvent or mixture thereof selected does not react with the organoaminodisilane. For certain embodiments, a composition comprising a tris(alkoxysilyl)amine or bis(alkoxysilyl)amine precursor and a compatible solvent may provide many advantages, compared to the pure tris(alkoxysilyl)amine or bis(alkoxysilyl)amine precursor. These advantages include: better usage of the tris(alkoxysilyl)amine or bis(alkoxysilyl)amine precursor in semiconductor processes, better stability over long term storage, cleaner evaporation by flash vaporization and overall more stable DLI chemical vapor deposition process. The amount of solvent by weight percentage in the composition ranges from 0.5% by weight to 99.5% or from 10% by weight to 75%. In this or other embodiments, the solvent has a boiling point (b.p.) similar to the b.p. of the tris(alkoxysilyl)amine and/or bis(alkoxysilyl)amine precursor or the difference between the b.p. of the solvent and the tris(alkoxysilyl)amine and/or bis(alkoxysilyl)amine precursor is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl) ether), or mixtures thereof. Further exemplary solvents for the composition include, but not limited to, octane (b.p. 125 to 126° C.), ethylcyclohexane (b.p. 130-132° C.), toluene (b.p. 115° C.), decane (b.p. 174° C.), and 2,2'-oxybis(N,N-dimethylethanamine (b.p., 189° C.).

In another embodiment, a vessel for depositing a silicon-containing film comprising one or more alkoxysilylamine having any one or Formulae A or B is described herein. In certain embodiments, the vessel comprises an interior to house the precursor and at least a portion of the interior surface that contacts the precursor is comprised of a liner which is made of a material selected from the group consisting of glass, plastic, metallic, plastic and combinations thereof. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the tris(alkoxysilyl)amine and/or bis(alkoxysilyl)amine precursor is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the alkoxysilylamine precursor having Formulae A and/or B and/or other precursor can be maintained in separate vessels or in a single vessel having separation means for maintaining the organoaminodisilane precursor and other precursor separate during storage.

In one embodiment of the method described herein, a cyclic deposition process such as CCVD, ALD, or PEALD may be employed, wherein at least one silicon-containing precursor selected from an alkoxysilylamine precursor having the formulae described herein and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments, the gas lines connecting from the precursor canisters to the reaction chamber are heated to one or more temperatures depending upon the process requirements and the container of the alkoxysilylamine precursor having the formulae A and/or B described herein is kept at one or more temperatures for bubbling. In other embodiments, a solution comprising the at least one silicon-containing precursor having the formulae A and/or B described herein is injected into a vaporizer kept at one or more temperatures for direct liquid injection.

A flow of argon and/or other gas may be employed as a carrier gas to help deliver the vapor of the at least one alkoxysilylamine precursor to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting silicon-containing film.

In another embodiment of the method disclosed herein, the films containing both silicon and nitrogen are formed using an ALD deposition method that comprises the steps of:
a. providing a substrate in an ALD reactor;
b. introducing into the ALD reactor an at least one (alkoxysilyl)amine precursor represented by the following Formulae A and B:

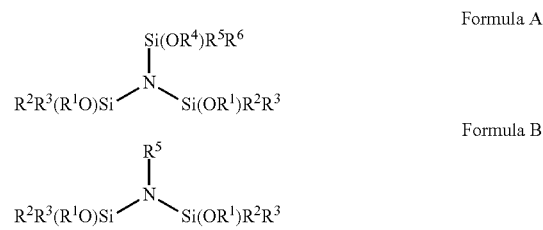

wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group;
c. chemisorbing the at least one alkoxysilylamine precursor onto a substrate;
d. purging away the unreacted at least one alkoxysilylamine precursor using a purge gas;
e. providing a nitrogen-containing source to the precursor onto the heated substrate to react with the sorbed at least one alkoxysilylamine precursor; and
f. optionally purging away any unreacted nitrogen-containing source.

In another embodiment of the method disclosed herein, the silicon-containing films is formed using an ALD deposition method that comprises the steps of:
a. providing a substrate in a reactor;
b. introducing into the reactor at least one alkoxysilylamine precursor represented by the following Formulae A and B:

Formula A

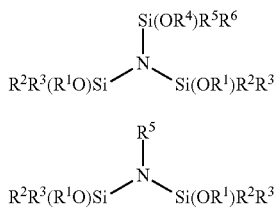

Formula B wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group;

c. chemisorbing the at least one at least one alkoxysilylamine precursor onto a substrate;

d. purging away the unreacted at least one at least one alkoxysilylamine precursor using a purge gas;

e. providing an oxygen source to the at least one alkoxysilylamine precursor onto the heated substrate to react with the sorbed at least one alkoxysilylamine precursor; and f. optionally purging away any unreacted oxygen source.

The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon-containing film, although always using oxygen in less than a stoichiometric amount relative to the available silicon.

For multi-component silicon-containing films, other precursors such as silicon-containing precursors, nitrogen-containing precursors, reducing agents, or other reagents can be alternately introduced into the reactor chamber.

In a further embodiment of the method described herein, the silicon-containing film is deposited using a thermal CVD process. In this embodiment, the method comprises:

(a) placing one or more substrates into a reactor which is heated to a temperature ranging from ambient temperature to about 700° C. and maintained at a pressure of 1 Torr or less;

(b) introducing at least one alkoxysilylamine precursor represented by the following Formulae A and B:

Formula A

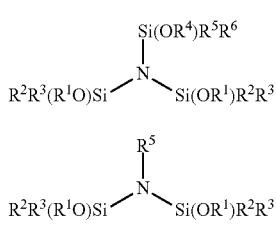

Formula B wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group; and (c) providing an oxygen source into the reactor to at least partially react with the a at least one alkoxysilylamine precursor and deposit a silicon-containing film onto the one or more substrates.

In a further embodiment of the method described herein, the silicon-containing film is deposited using a flowable CVD process. In this embodiment, the method comprises:

placing one or more substrates into a reactor which is heated to a temperature ranging from temperature below −20° C. to about 300° C. and maintained at a pressure of 1 Torr or less;

introducing at least one alkoxysilylamine precursor represented by the following Formulae A and B:

Formula A

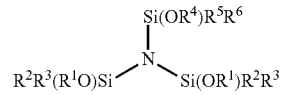

Formula B

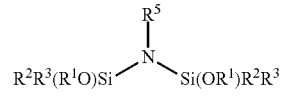

wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group;

providing a protonic source into the reactor to at least partially react with the at least one alkoxysilylamine precursor and deposit a silicon-containing film onto the one or more substrates;

optionally introducing a catalyst to promote the hydrolysis or net-work formation process; and subjecting the resulting film to one or more of the following treatments selected from vacuum, thermal, an oxidative using ozone, UV, water vapor, e-beam, plasma and combinations thereof to form a solid dielectric film.

Without being bound to theory, one embodiment for using the precursors described herein is a gap filling application wherein the incorporation of residual nitrogen in the form of a silicon nitride or oxynitride within as-deposited film can expand on subsequent oxidative treatment. This expansion ensure complete filling of gaps and re-entrant features and eliminates voiding or seams in high aspect ratio features. The protonic source can be selected from water, hydrogen peroxide, a mixture of water with other solvents including but not limited to alcohols, acetone, and THF. The catalyst can be selected from the group consisting of acids such as hydrogen chloride, carboxylic acids, halogen substituted carboxylic acids and bases such as ammonia, and organic amines. The acids or bases can be introduced into the reactor via various delivery methods or can be generated in situ via reaction of a chemical with the protonic source. Examples of catalysts include formic acid, acetic acid, trifluoroacetic acid, trichloroacetic acid, chloroacetic acid, triethylamine, diethylamine, n-propylamine, iso-propylamine, n-butylamine, t-butylamine, trifluoromethanesulfonic acid, and combinations thereof. The catalysts can also be selected from organic or inorganic compounds which can generate inorganic or organic acids upon hydrolysis. Examples of catalyst include metal or non-metal halides such as $BCl_3$, $AlCl_3$, $AlBr_3$, $Cl_2SO$, $PCl_3$, $OPCl_3$; carboxyl halide such as acetyl chloride, acetyl bromide; carboxylic anhydrides such as acetic anhydride.

In certain embodiments of the CVD method, the reactor is maintained at a pressure ranging from 100 mTorr to 600 mTorr during the introducing step. The above steps define one cycle for the method described herein; and the cycle can be repeated until the desired thickness of a silicon-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting silicon-containing film, although always using oxygen in less than a stoichiometric amount relative to the available silicon.

For multi-component silicon-containing films, other precursors such as silicon-containing precursors, nitrogen-containing precursors, oxygen sources, reducing agents, and/or other reagents can be alternately introduced into the reactor chamber.

In a further embodiment of the method described herein, the silicon-containing film is deposited using a thermal CVD process. In this embodiment, the method comprises:

a. placing one or more substrates into a reactor which is heated to a temperature ranging from ambient temperature to about 700° C. and maintained at a pressure of 1 Torr or less;

b. introducing at least one tris(alkoxysilyl)amine or bis(alkoxysilyl)amine or bis(alkoxysilyl)amine precursor represented by the following Formulae A and B:

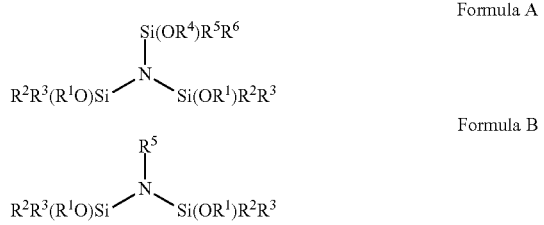

wherein $R^1$ and $R^4$ are independently selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$, $R^3$, $R^5$, and $R^6$ are independently selected from the group consisting of hydrogen, a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, a $C_6$ to $C_{10}$ aryl group, and a linear or branched $C_1$ to $C_{10}$ alkoxy group; and c. providing a nitrogen-containing source into the reactor to at least partially react with the at least one alkoxysilylamine precursor and deposit a silicon-containing film onto the one or more substrates.

In certain embodiments of the CVD method, the reactor is maintained at a pressure ranging from 100 mTorr to 600 mTorr during the introducing step.

In certain embodiments, the resultant silicon-containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon-containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon-containing film that is formed using the organoaminodisilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to 50%; and H ranges from about 0% to about 50% atomic percent weight % wherein x+y+z+v+w=100 atomic weight percent, as determined for example, by XPS or other means.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nano-electromechanical systems, thin film transistor (TFT), and liquid crystal displays (LCD).

The following examples illustrate the method for preparing alkoxyaminosilane precursors as well as deposited silicon-containing films described herein and are not intended to limit it in any way.

EXAMPLES

Example 1

Synthesis of tris(dimethoxysilyl)amine

A quantity of 400 milliliters (ml) hexane and 200 grams (g) trichlorosilane were added to a 1000 ml three-necked round bottom flask equipped with an addition funnel, a condenser, a mechanical stirrer, a gas inlet and a gas outlet. With mechanical stirring, the solution was cooled to −30° C. with a dry ice isopropylalcohol (IPA) bath. A quantity of 96 g anhydrous methanol was added dropwise through the addition funnel. Generated HCl gas was introduced through the gas outlet into a flask containing water for absorption. After the addition of anhydrous methanol and HCl gas, was completed, the reaction mixture was allowed to warm to room to room temperature slowly with stirring. The stirring continued at room temperature for 2 hours. Then nitrogen was bubbled through the reaction mixture to purge out residual HCl. Gas chromatography mass spectra (GC-MS) showed the major product was dimethoxychlorosilane.

The dimethoxychlorosilane solution in hexane was cooled to −20° C. With stirring, anhydrous ammonia was bubbled through the solution. A white precipitate of ammonium chloride gradually formed. The reaction was monitored with GC-MS. Once the reaction was complete, the reaction mixture was allowed to warm up to room temperature. Ammonium chloride was removed by filtration. GC-MS of the solution showed the major product was 1,1,3,3-tetramethoxydisilazane. Approximately 1 equivalent of 1,1,3,3-tetramethoxydisilazane solution in hexane and 1.05 equivalent triethylamine were added to a three-necked round bottom flask equipped with an addition funnel, a condenser, and a mechanical stirrer. With stirring, 1 equivalent of dimethoxychlorosilane made in step 1 was added slowly through the addition funnel. The reaction mixture was stirred at room temperature for 24 hours. Triethylamine hydrochloride salt was removed by filtration. Hexane was removed by distillation at ambient pressure. Tris(dimethoxysilyl)amine was isolated by vacuum distillation. The mass spectroscopy showed the product with the molecular weight of 287 and is provided herein as FIG. 1. The MS peaks for tris(dimethoxysilyl)amine are provided in Table I.

Example 2

Synthesis of bis(diethoxysilyl)amine (Formula B) and tris(diethoxysilyl)amine (Formula A)

In a 250 mL 3-neck flask, 107 g of trichlorosilane was loaded and cooled in an isopropyl alcohol/dry ice bath at −50° C. In an additional funnel, 73.6 g of anhydrous ethanol was loaded and added drop-wise to the trichlorosilane at −50° C. After the addition was complete, the solution was slowly warmed to room temperature and allowed to stir overnight. The resulting diethoxychlorosilane was then transferred to a 1000 mL 3-neck flask. 500 mL of hexanes was added to the flask and the diethoxychlorosilane solution was stirred with a mechanical stirrer. Anhydrous ammonia was then introduced to the diethoxychlorosilane solution. Upon completion, the reaction mixture was allowed to warm to room temperature and stirred overnight. The reaction mixture was then filtered to remove the solid by-product. GC-MS of the mixture shows evidence of the disilazane compound with a M−1 peak at 252 amu as well as evidence of the tris-silylamine compound with a M−1 peak at 370 amu. Simple distillation was performed to remove hexanes. Vacuum distillation was performed to purify the bis-silylamine product. Boiling point of the product was observed to be 102° C. at 8-9 Torr and the yield was 69%. Further MS peaks as well as the molecular weight for each end-product is provided in Table I.

Example 3

Synthesis of bis(dimethoxysilyl)amine (Formula B) and tris(dimethoxysilyl)amine (Formula A)

In a 250 mL 3-neck flask, 164.4 g of trichlorosilane was loaded and cooled in an isopropyl alcohol/dry ice bath at −20° C. In an additional funnel, 77.8 g of anhydrous methanol was loaded and added drop-wise to the trichlorosilane at −20° C. After the addition was complete, the solution was slowly warmed to room temperature and allowed to stir overnight. The resulting dimethoxychlorosilane was then transferred to a 1000 mL 3-neck flask. 500 mL of hexanes was added to the flask and the dimethoxychlorosilane solution was stirred with a mechanical stirrer. Anhydrous ammonia was then introduced to the dimethoxychlorosilane solution. Upon completion, the resulting reaction mixture was allowed to warm to room temperature and stirred overnight. The reaction mixture was then filtered to remove the solid by-product. GC-MS of the mixture shows evidence of the bis-silylamine compound with a M−1 peak at 196 amu as well as evidence of the tris-silylamine compound with a strong molecular ion peak at 271 amu. Further MS peaks as well as the molecular weight for each end-product is provided in Table I.

Example 4

Synthesis bis(methoxymethylsilyl)amine (Formula B) and tris(methoxymethylsilyl)amine (Formula A)

To a solution of 104.0 g (904.08 mmol) dichloromethylsilane in hexanes at −20° C. was added 29.0 g (904.08 mmol) of anhydrous methanol drop-wise via an additional funnel. The resulting mixture was purged several hours with argon to remove HCl by-product. Next, ammonia was bubbled through the mixture at 0° C. in three separate increments to produce a total of 25 g of a white solid that was filtered from the reaction mixture. GC-MS of the mixture shows evidence of the bis-silylamine compound with a parent peak at 165 amu as well as of the tris-silylamine compound with a strong fractional peak at 224 amu. The boiling point of the bis-silylamine compound was observed at 55° C. at 20 Torr. Further MS peaks as well as the molecular weight for each end-product is provided in Table I.

Example 5

Synthesis of N-iso-propylbis(diethoxysilyl)amine (Formula B)

To a solution of 1.00 g (7.38 mmol) of trichlorosilane in 3 mL of hexanes at room temperature was added 0.68 g (14.77 mmol) of anhydrous ethanol. Witnessed vigorous bubbling that subsided after 20 minutes and the reaction was purged with nitrogen to remove HCl by-product for one hour. Next, a solution of 0.22 g (3.69 mmol) isopropylamine and 0.75 g (7.38 mmol) triethylamine in 4 mL of hexanes was added slowly and a white precipitate was immediately formed. A sample was filtered and run on GC-MS and showed a strong fraction peak at 280 amu. Further MS peaks as well as the molecular weight for each end-product is provided in Table I.

TABLE 1

Exemplary Compounds having Formulae A and B and their MS peaks

| No. | Compounds | MW | Structure | MS Peaks |
|---|---|---|---|---|
| 1 | Bis(diethoxysilyl)amine | 253.44 | EtO–Si(H)(OEt)–N(H)–Si(H)(OEt)–OEt | 252, 224, 208, 180, 164, 140, 124, 106, 90, 62 |

TABLE 1-continued

Exemplary Compounds having Formulae A and B and their MS peaks

| No. | Compounds | MW | Structure | MS Peaks |
|---|---|---|---|---|
| 2 | Bis(dimethoxysilyl)amine | 197.34 | 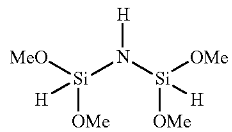 [SMILES: CO[SiH](N[SiH](OC)OC)OC] | 196, 182, 166, 152, 136, 123, 106, 90, 76, 59 |
| 3 | N-iso-propylbis(diethoxysilyl)amine | 295.52 | 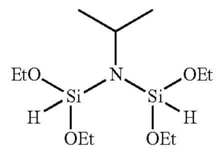 [SMILES: CCO[SiH](OCC)N(C(C)C)[SiH](OCC)OCC] | 294, 280, 265, 250, 234, 220, 209, 181, 165, 153, 137, 125, 109, 91, 63 |
| 4 | Bis(methoxymethylsilyl)amine | 165.34 | 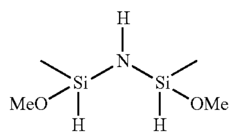 | 165, 150, 134, 120, 104, 90, 75, 59, 45 |
| 5 | Tris(dimethoxysilyl)amine | 287.49 | 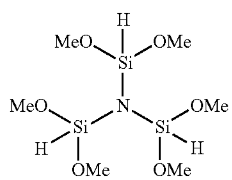 [SMILES: CO[SiH](OC)N([SiH](OC)OC)[SiH](OC)OC] | 271, 257, 239, 225, 209, 195, 179, 165, 150, 136, 119, 104, 91, 76, 59 |
| 6 | Tris(diethoxysilyl)amine | 371.65 | 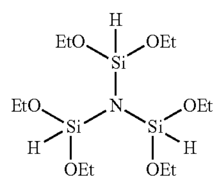 [SMILES: CCO[SiH](OCC)N([SiH](OCC)OCC)[SiH](OCC)OCC] | 370, 326, 309, 296, 282, 268, 252, 240, 224, 208, 196, 180, 166, 156, 138, 122, 105, 91, 78, 60, 50 |
| 7 | Tris(methoxymethylsilyl)amine | 239.49 | 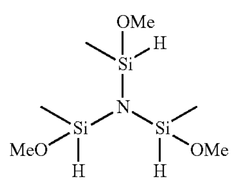 | 224, 210, 192, 177, 161, 147, 133, 117, 103, 86, 75, 59, 45 |

The invention claimed is:

1. A precursor comprising at least one compound selected from the group consisting of ((MeO)$_2$HSi)$_2$NH, ((EtO)$_2$HSi)$_2$NH, ((MeO)$_2$MeSi)$_2$NH, ((EtO)$_2$MeSi)$_2$NH, ((MeO)MeHSi)$_2$NH, ((EtO)MeHSi)$_2$NH, ((MeO)$_2$HSi)$_2$NMe, ((EtO)$_2$HSi)$_2$NMe, ((MeO)$_2$MeSi)$_2$NMe, ((EtO)$_2$MeSi)$_2$NMe, ((MeO)MeHSi)$_2$NMe, ((EtO)MeHSi)$_2$NMe, ((MeO)$_2$HSi)$_2$NEt, ((EtO)$_2$HSi)$_2$NEt, ((MeO)$_2$MeSi)$_2$NEt, ((EtO)$_2$MeSi)$_2$NEt, ((MeO)MeHSi)$_2$NEt, ((EtO)MeHSi)$_2$NEt, ((MeO)$_2$HSi)$_2$NPr$^n$, ((EtO)$_2$HSi)$_2$NPr$^n$, ((MeO)$_2$MeSi)$_2$NPr$^n$, ((EtO)$_2$MeSi)$_2$NPr$^n$, ((MeO)MeHSi)$_2$NPr$^n$, ((EtO)MeHSi)$_2$NPr$^n$, ((MeO)$_2$HSi)$_2$NPr$^i$, ((EtO)$_2$HSi)$_2$NPr$^i$, ((MeO)$_2$MeSi)$_2$NPr$^i$, ((EtO)$_2$MeSi)$_2$NPr$^i$, ((MeO)MeHSi)$_2$NPr$^i$, ((EtO)MeHSi)$_2$NPr$^i$, ((MeO)$_2$HSi)$_2$NBu$^t$, ((EtO)$_2$HSi)$_2$NBu$^t$, ((MeO)$_2$MeSi)$_2$NBu$^t$, ((EtO)$_2$MeSi)$_2$NBu$^t$, ((MeO)MeHSi)$_2$NBu$^t$, ((EtO)MeHSi)$_2$NBu$^t$, ((EtO)$_2$HSi)$_3$N, ((MeO)MeHSi)$_3$N, ((EtO)MeHSi)$_3$N, ((MeO)$_2$HSi)$_2$NSiH$_2$(OBu$^t$), ((EtO)$_2$HSi)$_2$NSiH$_2$(OBu$^t$), ((MeO)$_2$HSi)$_2$NSiH(OEt)$_2$, ((MeO)$_2$HSi)$_3$N, ((EtO)$_2$HSi)$_3$N, ((MeO)MeHSi)$_3$N, ((EtO)MeHSi)$_3$N, ((MeO)$_2$HSi)$_2$NSiH$_2$(OBu$^t$), ((EtO)$_2$HSi)$_2$NSiH$_2$(OBu$^t$), ((MeO)$_2$HSi)$_2$NSiH(OEt)$_2$, and (($^t$BuO)H$_2$Si)$_3$N.

2. The precursor of claim 1 wherein the compound is tris(diethoxysilyl)amine.

* * * * *